US009710600B1

(12) United States Patent
Dunleavy et al.

(10) Patent No.: US 9,710,600 B1
(45) Date of Patent: Jul. 18, 2017

(54) HEALTHCARE GAP MANAGEMENT SYSTEM (71) Applicant: Inovalon, Inc., Bowie, MD (US)

(72) Inventors: Keith R. Dunleavy, Annapolis, MD (US); Daniel Rizzo, Annapolis, MD (US)

(73) Assignee: Inovalon, Inc., Bowie, MD (US)

( * ) Notice: Subject to any disclaimer, the term of this patent is extended or adjusted under 35 U.S.C. 154(b) by 0 days.

(21) Appl. No.: 14/886,876

(22) Filed: Oct. 19, 2015

Related U.S. Application Data (60) Provisional application No. 62/065,218, filed on Oct. 17, 2014.

(51) Int. Cl.
*G06Q 50/22* (2012.01)
*G06Q 50/24* (2012.01)
*G06F 19/00* (2011.01)

(52) U.S. Cl.
CPC ........ *G06F 19/322* (2013.01); *G06F 19/3487* (2013.01)

(58) Field of Classification Search
CPC ......... G06Q 50/22; G06Q 50/24; G06Q 10/10
See application file for complete search history.

(56) References Cited

U.S. PATENT DOCUMENTS

| 7,260,480 | B1 | 8/2007 | Brown et al. |
| 7,590,550 | B2 | 9/2009 | Schoenberg |
| 2004/0128163 | A1 | 7/2004 | Goodman et al. |
| 2006/0047539 | A1 | 3/2006 | Huang |
| 2009/0254368 | A1 | 10/2009 | Cunnold |
| 2015/0066539 | A1* | 3/2015 | Sheffer ................ G06F 19/345 705/3 |
| 2016/0012187 | A1* | 1/2016 | Zasowski ............... G06Q 10/10 705/3 |

* cited by examiner

*Primary Examiner* — Maroun Kanaan
(74) *Attorney, Agent, or Firm* — Fish & Richardson P.C.

(57) ABSTRACT

Methods, systems, and apparatus, including computer programs encoded on non-transitory computer readable storage media, for integrating with an electronic health record system to permit healthcare providers, health insurance companies, and healthcare analytics providers to manage healthcare gaps in real-time.

20 Claims, 4 Drawing Sheets

HEALTHCARE GAP MANAGEMENT SYSTEM

CROSS-REFERENCE TO RELATED APPLICATION

This application claims the benefit of U.S. Provisional Patent Application No. 62/065,218, filed Oct. 17, 2014, which is incorporated herein by reference.

TECHNICAL FIELD

The present disclosure relates to integrating a healthcare gap management process with an electronic medical record system in real-time.

BACKGROUND

An electronic health record ("EHR") is a systematic collection of electronic health information about a healthcare consumer (e.g., a patient, or "member"). An EHR may be capable of being shared across different healthcare settings. In some cases this sharing can occur by way of network-connected, enterprise-wide information systems and other information networks or exchanges. EHRs may include a range of data, including demographics, medical history, medication and allergies, immunization status, laboratory test results, radiology images, vital signs, personal statistics like age and weight, and billing information.

SUMMARY

A system as described in the present disclosure integrates with an electronic health record system to permit healthcare providers, health insurance companies, and healthcare analytics providers to manage healthcare gaps in real-time. As used by this specification, a "healthcare gap" refers to a gap in clinical quality, care, assessment, documentation, waste avoidance, data accuracy, or compliance.

In general, one innovative aspect of the subject matter described in this specification can be embodied in a non-transitory computer-readable medium storing instructions executable by one or more computers which, upon execution, cause the one or more computers to perform operations that include receiving, at a data analytics provider system from a healthcare provider system over a network, an encounter start notification identifying a patient, the encounter start notification being received in real-time when the patient begins an encounter with a healthcare provider, determining, at the data analytics provider system, that one or more healthcare gaps are present for the patient, providing, from the data analytics provider system, data indicating that healthcare gaps are present for the patient, and receiving, at the data analytics provider system, a request for a set of healthcare gaps associated with the patient. The operations also include providing, from the data analytics provider system to the healthcare provider system, data representing the set of healthcare gaps associated with the patient, wherein the set of healthcare gaps includes at least one entry to be associated with an electronic health record of the patient such that the healthcare provider system can indicate whether one or more of the healthcare gaps was addressed, receiving, at the data analytics provider system, an encounter end notification indicating that the healthcare provider system addressed one or more of the set of healthcare gaps, and initiating an update of the electronic health record of the patient in real-time based on the one or more of the set of healthcare gaps being addressed.

Implementations may include one or more of the following features. The encounter start notification may include one or more of an electronic health record practice identifier, an electronic health record provider identifier, and a patient identifier. The encounter end notification may include one or more of an electronic health record practice identifier, an electronic health record provider identifier, and a patient identifier.

Determining, at the data analytics provider system, that one or more healthcare gaps are present for the patient may include querying a healthcare database to determine that one or more healthcare gaps are present for the patient.

In general, another innovative aspect of the subject matter described in this specification can be embodied in a non-transitory computer-readable medium storing instructions executable by one or more computers which, upon such execution, cause the one or more computers to perform operations that include providing, from a healthcare provider system to a data analytics provider system over a network, an encounter start notification identifying a patient in real-time when the patient begins an encounter with a healthcare provider, receiving, at the healthcare provider system, data indicating that healthcare gaps are present for the patient, providing, from the healthcare provider system, a request for a set of healthcare gaps associated with the patient, receiving, at the healthcare provider system, data representing the set of healthcare gaps associated with the patient, wherein the set of healthcare gaps includes at least one entry to be associated with an electronic health record of the patient such that a user of the healthcare provider system can indicate whether one or more of the healthcare gaps was addressed, and providing, from the healthcare provider system, an encounter end notification in real-time when the patient ends the encounter with the healthcare provider, the encounter end notification indicating that the healthcare provider system addressed one or more of the set of healthcare gaps.

Implementations may include one or more of the following features. The encounter start notification may include one or more of an electronic health record practice identifier, an electronic health record provider identifier, and a patient identifier. The encounter end notification may include one or more of an electronic health record practice identifier, an electronic health record provider identifier, and a patient identifier.

The operations may further include providing for display data representing the set of healthcare gaps. The operations may further include determining that at least one healthcare gap from the set of healthcare gaps has been addressed. The one or more healthcare gaps include a gap in care. Alternatively, the one or more healthcare gaps include a gap in documentation.

In general, another innovative aspect of the subject matter described in this specification can be embodied in a data analytics provider system that includes one or more computers and one or more storage devices storing instructions that are operable, when executed by the one or more computers, to cause the one or more computers to perform operations that include receiving, at the data analytics provider system from a healthcare provider system over a network, an encounter start notification identifying a patient, the encounter start notification being received in real-time when the patient begins an encounter with a healthcare provider; determining, at the data analytics provider system, that one or more healthcare gaps are present for the patient;

providing, from the data analytics provider system, data indicating that healthcare gaps are present for the patient; receiving, at the data analytics provider system, a request for a set of healthcare gaps associated with the patient; providing, from the data analytics provider system to the healthcare provider system, data representing the set of healthcare gaps associated with the patient, wherein the set of healthcare gaps includes at least one entry to be associated with an electronic health record of the patient such that the healthcare provider system can indicate whether one or more of the healthcare gaps was addressed; receiving, at the data analytics provider system, an encounter end notification indicating that the healthcare provider system addressed one or more of the set of healthcare gaps; and initiating an update of the electronic health record of the patient in real-time based on the one or more of the set of healthcare gaps being addressed.

Implementations may include one or more of the following features. The encounter start notification may include one or more of an electronic health record practice identifier, an electronic health record provider identifier, and a patient identifier. The encounter end notification may include one or more of an electronic health record practice identifier, an electronic health record provider identifier, and a patient identifier.

In general, another innovative aspect of the subject matter described in this specification can be embodied in a healthcare provider system that includes one or more computers and one or more storage devices storing instructions that are operable, when executed by the one or more computers, to cause the one or more computers to perform operations that include providing, from the healthcare provider system to a data analytics provider system over a network, an encounter start notification identifying a patient in real-time when the patient begins an encounter with a healthcare provider; receiving, at the healthcare provider system, data indicating that healthcare gaps are present for the patient; providing, from the healthcare provider system, a request for a set of healthcare gaps associated with the patient; receiving, at the healthcare provider system, data representing the set of healthcare gaps associated with the patient, wherein the set of healthcare gaps includes at least one entry to be associated with an electronic health record of the patient such that a user of the healthcare provider system can indicate whether one or more of the healthcare gaps was addressed; and providing, from the healthcare provider system, an encounter end notification in real-time when the patient ends the encounter with the healthcare provider, the encounter end notification indicating that the healthcare provider system addressed one or more of the set of healthcare gaps.

Implementations may include one or more of the following features. The encounter start notification may include one or more of an electronic health record practice identifier, an electronic health record provider identifier, and a patient identifier. The encounter end notification may include one or more of an electronic health record practice identifier, an electronic health record provider identifier, and a patient identifier.

The operations may further include providing for display data representing the set of healthcare gaps. The operations may further include determining that at least one healthcare gap from the set of healthcare gaps has been addressed. The one or more healthcare gaps may include a gap in care.

Particular embodiments of the subject matter described in this specification can be implemented so as to realize one or more of the following advantages. By providing real-time notifications to healthcare providers, and real-time updates to EHRs, the subject matter described in this specification may improve the technical field of healthcare management. Conventional systems that rely on human reviewers to identify healthcare gaps and send notifications to healthcare providers and/or patients may incur significant omissions, delays, inefficiencies, and inaccuracies. In addition, the real-time nature of the updates described in this specification may allow healthcare gaps to be updated automatically when healthcare treatment protocols are updated or added. Moreover, conventional systems may not be able to scale easily to handle the large volumes of data involved in managing hundreds or thousands of patients and EHRs. In contrast, embodiments described in this specification may be able to readily scale to address such volumes of data in real-time. For example, embodiments described in this specification may be able to perform millions of transactions within a very short period of time.

The details of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Electronic health record (EHR) interoperability is a ground-breaking capability initiative that takes an agnostic approach to creating a nationally scalable framework that meets the needs of nearly every participant within the healthcare continuum. It uses targeted patient-specific analytics to deliver point-of-care quality, risk, utilization and medical history insights that directly impacts healthcare quality outcomes and financial performance. Despite billions of U.S. dollars spent on interoperability to-date, payers and providers do not have an efficient and effective means of sharing both aggregate and detailed patient-level performance data. Entities and organizations, including individual clinicians, health plans, hospital systems, integrated health care delivery systems, Accountable Care Organizations, physician organizations, CMS, state agencies, payers, other managed care organizations, and provider entities which share in the risk and incentives around care, quality, disease severity, utilization, and compliance, continue to struggle to achieve efficient means of collecting information needed from the provider community; and methods of regulation-driven initiatives focused on quality, utilization, and compliance for applicable patients. Providers, including hospitals and physician groups, continue to struggle with what data to collect and share back with other organizations; and how to execute upon the myriad of requested quality, utilization, and compliance goals.

EHR interoperability embeds patient-specific gaps into the encounter at the point of care within the provider's EHR system while also enabling the automation of medical record data capture. Upon receiving the provider group's authorization, which may be obtained in a manner which need only be a one-time event, systems as described in this specification may automatically retrieve targeted medical record data for quality and risk score accuracy from a centrally maintained repository from each EHR partner. Analytical systems identify gaps in care, quality, risk score accuracy, cost efficiency, and compliance that are embedded directly into EHR partners' workflow systems. Gap resolution alerts empower the point of care through integrated EHR systems.

Direct EHR interoperability facilitates significant quality of care, speed, financial, accuracy, and accessibility benefits while decreasing provider disruption and network friction.

The disclosure herein describes exemplary EHR partnership models. For example, data analytics providers can work directly with a hospital system to develop a plug-in that permits encrypted communication between the data analytics provider's EHR system and the hospital's EHR system. Or using its various EHR vendor partnerships can facilitate communication between an interoperability platform and the hospital's EHR system. This communication channel will facilitate a transparent medical record data retrieval process.

The interoperability platform as described in this specification is an information pathway to serve all those engaged in the delivery and management of care. The platform enables electronic records from acute, ambulatory, cloud based, thick or thin clients to be seamlessly integrated to offer a holistic, comprehensive reflection into the medical history and current condition of a patient. This enables doctors, hospitals and physician groups with timely, accurate and complete information that supports care management and the continuum of care. Patient safety is increased by aiding in the facilitation of the right and most appropriate diagnostics, assessments, and treatment plans. Patient data may be stored and communicated in an encrypted form, improving data security and minimizing the probability of an unintended disclosure of personal information. The overall quality of care, management of care and population health can be consequently improved. Such a service brings together electronic records agnostic to the underlying system offers the medical community actionable insights that includes everything from allergies to a complete listing of diagnosis that truly empower sharing of medical information.

As an overview, by analyzing EHRs and other data sources such as claims data, pharmacy data, laboratory data, etc., a healthcare insurance plan, healthcare professional, or other entity may recognize that a patient is not in compliance with treatment protocols, best practices, or guidelines (i.e., identification of a "gap"). For example, a gap in care may represent a difference between a recommended treatment protocol and an actual course of treatment for a diagnosed condition. A gap in documentation may represent a difference between an actual course of treatment and a diagnosis that corresponds to that course of treatment (e.g., a patient has received treatments that do not correspond to any recorded diagnosis). The gap analysis may be determined retrospectively by analyzing historic data or prospectively through the undertaking of various predictive analytical processes, e.g., by applying patent information to a rule-based system, a classifier, a support vector machine, or an artificial neural network.

When a healthcare gap is identified, the health insurance plan or other entity may want to identify the healthcare gap to a healthcare provider. For example, in some cases, a healthcare gap may be rectified by initiating an encounter between the healthcare provider and a patient (a "patient encounter"). However, conventional techniques of notifying healthcare providers, such as telephone calls, manual email, or mail reminders may be cost prohibitive or ineffective. Other conventional techniques may involve sending updates and notifications directly to a patient to request that the clinician address healthcare gaps. However, direct communications with the clinician may also be ineffective because they rely on the patient to schedule appointments and perform other actions, thus compliance may be low. To overcome some of the deficiencies of conventional techniques, a system that integrates a gap management process with EHRs in real-time is described in the present disclosure. As described in this specification, "real-time" refers to an action that occurs contemporaneously or nearly contemporaneously (e.g., within several seconds of) with another event.

Figure 1:
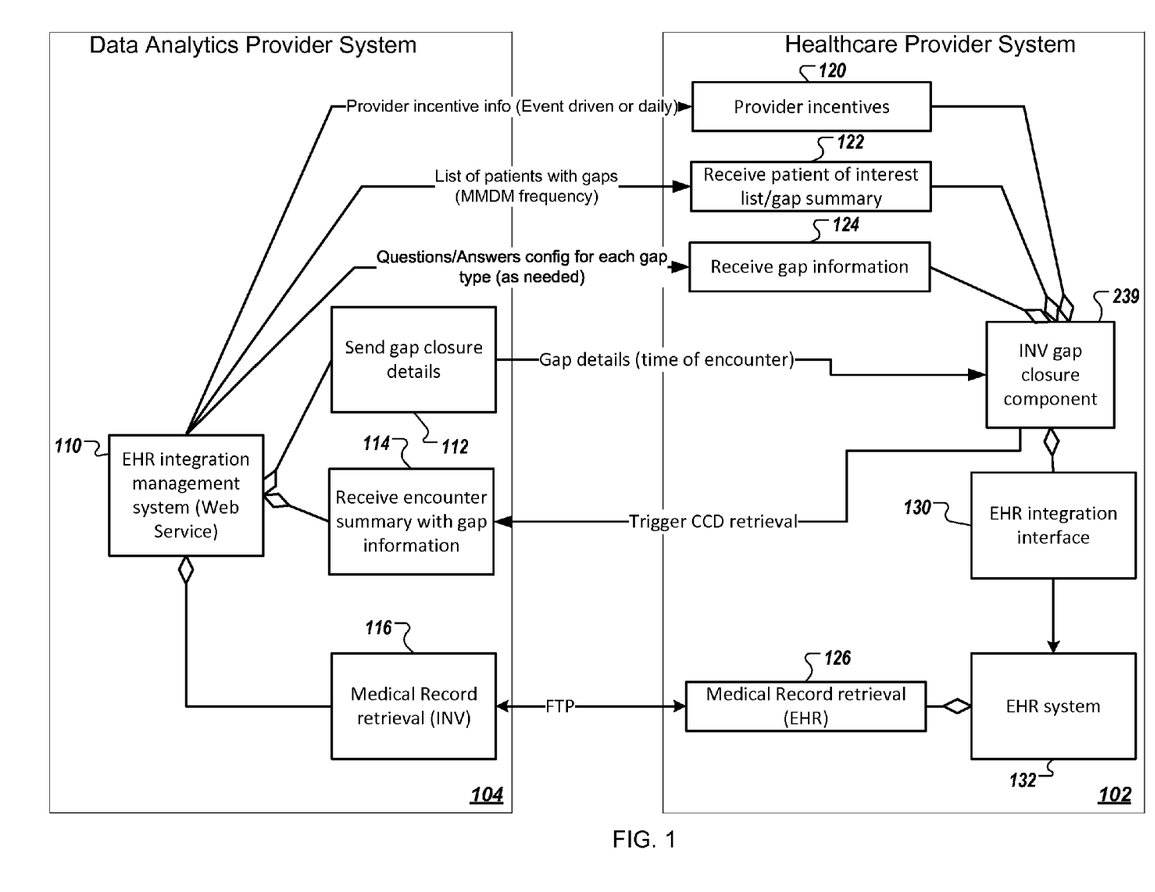
FIG. 1 is an example of a healthcare gap management system.

As an overview, a gap management system 100 involves an ongoing process of real-time interactions that provides a variety of functionality. The system may involve a healthcare provider system 102 that communicates with a data analytics provider system 104, e.g., in encrypted form, via a network such as the Internet. The healthcare provider system 102 may be, for example, a server or set of servers that include an EHR system 106, or a medical device or item of medical diagnostic equipment operated by the healthcare provider. The data analytics provider system 104 may also be a server or set of servers that identify gaps based on analysis of EHRs, or may be implemented by medical diagnostic equipment.

FIG. 1 shows an example of such a gap management system 100. In FIG. 1, the healthcare provider system 102 hosts an EHR system 132 and several application programming interface (API) endpoints. The API endpoints may include a provider incentives endpoint 120 that receives provider incentive information (e.g., on an event driven or daily basis); a receive patient of interest list/gap summary endpoint 122 that receives a list of patients with gaps; and a receive gap definition endpoint 124 that receives questions/answers configuration information for each gap type as needed. These three endpoints access a gap closure component 128, which is a skinnable component to manage questions and answers and to facilitate integration with the EHR system 132. The gap closure component 128 communicates with an EHR integration interface 130, which in turn interoperates with the EHR system 132. The healthcare provider system 102 also includes a medical record retrieval endpoint 128 that provides access to the EHR records.

The data analytics provider system 104 accesses the API endpoints of the healthcare provider system 102. The data analytics provider system 104 includes an endpoint 112 that transmits gap closure details to the gap closure component 128 of the healthcare provider system 102, a receive encounter summary with gap information endpoint 114, and a medical record retrieval endpoint 116 that accesses the EHR system 132 of the healthcare provider system 102 via the medical record retrieval endpoint 126. The data analytics provider system 104 also includes an EHR integration management system 110 that includes business logic for managing the endpoints.

Figure 2:
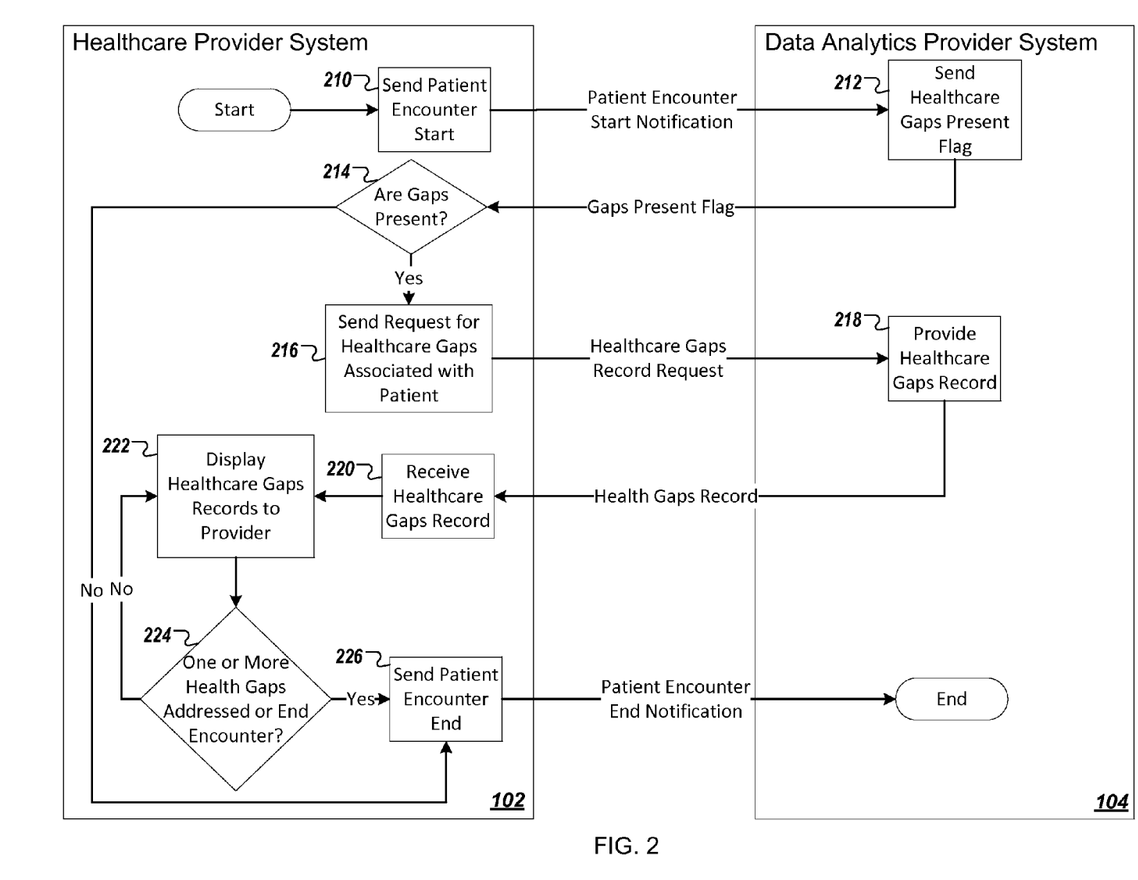
FIG. 2 is an example of a process for real-time healthcare gap management.

In an example operation illustrated in FIG. 2, the gap management process begins with an "Encounter Start" notification in stage 210. When a patient visits a healthcare provider that is registered with the data analytics provider system 104, the healthcare provider system 102 transmits a message indicating that a patient encounter has begun. For example, when a patient visits the office of a doctor registered with the data analytics provider system 104 and checks in, a doctor, nurse, or nurse practitioner may log the patient's visit using a client device. The client device may include one or more processing devices, and may be, or include, a mobile telephone (e.g., a smartphone), a laptop computer, a handheld computer, a tablet computer, a network appliance, or a combination of any two or more of these data processing devices or other data processing devices. Alternatively, a mobile device associated with the patient may detect, e.g., using a global positioning system (GPS) sensor, a Wi-Fi sensor, or a beacon detector, that its location matches a location that is associated with the office of the doctor, thereby triggering the "Encounter Start" notification.

The client device may communicate with the healthcare provider system 102, which may include a number of different devices, for example a cloud-based system, "anything as a service" (XaaS) system, a standard server, a group of such servers, or a rack server system, and may be accessed via any network such as the Internet, a wired or wireless local area network (LAN), wide area network (WAN), etc. The healthcare provider system 102 may automatically initiate the patient encounter start notification. This message may include various data identifying the provider and/or the patient such as an EHR practice ID, an EHR provider ID, and a patient ID.

In stage 212, in response to the patient encounter start notification, the data analytics provider system 104 may transmit a message back to the healthcare provider system 102 indicating that either: (i) the patient has healthcare gaps or (ii) the patient does not have any healthcare gaps. This message may be, for example, a flag that represents either "healthcare gaps present flag" or "no healthcare gaps present flag."

In stage 214, the healthcare provider system 102 determines whether any gaps are present based on the flag. The healthcare provider system 102 then may access an API provided by the data analytics provider system 104 to obtain details of any gaps. For example, upon receiving a healthcare gaps present flag for the patient of a specific ongoing patient encounter, in stage 216 the healthcare provider system 102 may request a healthcare gaps record associated with the patient via a data analytics provider system API (the "data analytics provider gap management API"). The data analytics provider system 104 then provides the requested healthcare gaps record to the healthcare provider system in stage 218. The healthcare provider system 102 then receives the healthcare gaps record in stage 220 and displays a list of healthcare gaps (the "healthcare gap list") within a displayed dialog box or window (the "healthcare gap list notification dialog") in stage 222. The healthcare gap list notification dialog will reference the healthcare gap list with specific language provided by data analytics provider system 104 and will have a suitable graphic layout. Notably, the healthcare gap list is displayed before the patient's encounter has ended, e.g., when the patient ends their visit to the healthcare provider, or upon determining that the encounter is soon likely to end.

If gaps exist, the graphic layout may dynamically adjust to include a region for displaying the returned gap information and, for each gap, may include a selectable control for allowing a user to obtain additional information regarding each gap. Through the data analytics provider gap management API, a user of the healthcare provider system 102 may select individual healthcare gaps to be displayed with the healthcare gap list notification dialog.

When an individual healthcare gap is selected by the healthcare provider system 102, the data analytics provider gap management API will provide a dialog (the "healthcare gap dialog") unique to the patient and respective selected healthcare gap. The healthcare gap dialog will reference the healthcare gap with specific language provided by data analytics provider system 104 to address and potentially resolve such a healthcare gap. As the user of the healthcare provider system 102 selects individual entries within the healthcare gap list and interacts with the individual healthcare gap dialogs, the data analytics provider system 104 will provide to the healthcare provider system 102 a specific system action within the EHR provider system 132 (each a "system action direction"). The system action directions may include the following.

Make Entry Within EHR: The data analytics provider system 104 may provide data detailing a section of the EHR (e.g., history of present illness, vital signs, assessment/impression, plan, or other such sections), text entry content (the respective system action direction's "text content"), and associated reference hash tag (the respective system action direction's "reference tag") to be recorded within the patient encounter record and its associated metadata respectively, and the healthcare provider system 102 may place the text content and reference tag within the patient encounter record in real-time.

Order Test From EHR: The data analytics provider system 104 may provide data detailing a type of test (e.g., laboratory, radiological, or other such test which may be ordered by or from the healthcare provider system 102) to be ordered, and healthcare provider system 102 may navigate to and present appropriate screens/interfaces to enable healthcare provider system 102 to order the test in real-time. Once approved, the data analytics provider system 104 or the healthcare provider system 102 may interact directly with medical diagnostic equipment to schedule or initiate performance of the additional test.

Order Prescription from EHR: The data analytics provider system 104 may provide data detailing a pharmacy prescription (e.g., medication type) to be ordered, and the healthcare provider system 102 may navigate to and present appropriate screens/interfaces to enable the healthcare provider system 102 to order the prescription in real-time. Once approved, the data analytics provider system 104 or the healthcare provider system 102 may interact directly with a pharmacy computing system, to initiate an order for the pharmacy prescription.

Make Referral From EHR: The data analytics provider system 104 may provide data detailing a type of referral (e.g., cardiology, endocrinology, or other such referral that may be made by or from the healthcare provider system 102) to be ordered, and the healthcare provider may navigate to and view appropriate screens/interfaces to enable the healthcare provider system 102 to make the referral in real-time. Once approved, the data analytics provider system 104 or the healthcare provider system 102 may interact directly with a computing system associated with the recipient of the referral, to initiate scheduling of an appointment.

In some implementations, the data analytics provider system 104 may also modify or describe additional system action directions. Also, within the healthcare provider system 102, the text content may be editable by the EHR system 132 during the patient encounter; however, in some implementations the reference tag may not be editable.

Encounter End Notification: Upon the completion of a patient encounter, the healthcare provider system 102 may facilitate the provision to the data analytics provider system 104, in real-time, of notification (the "patient encounter end notification") consisting of the EHR practice ID, EHR provider ID, patient identifier set, and an indication as to whether the EHR provider validly signed the encounter (together, the "patient encounter end notification data set"). For example, the healthcare provider system 102 may determine whether the health gaps have been addressed and/or whether the patient encounter has ended, or the healthcare provider system 102 or the data analytics provider system may determine that the encounter is soon likely to end, in stage 224. If so, then the healthcare provider system 102 sends the patient encounter end notification to the data analytics provider system 104 in stage 226. If not, then the healthcare provider system may return to stage 222 and display additional healthcare gaps records.

Intervention Commitment Notification: Upon any system action direction being implemented within the healthcare provider system 102 and the associated EHR system 132 acknowledging such implementation, the healthcare provider system 102 may facilitate the provision to the data analytics provider system 104, in real-time, of notification (the "EHR system action commitment notifications") consisting of the EHR practice ID, EHR provider ID, and a patient identifier set, as to the system action direction that was successfully implemented and acknowledged by the EHR system 132 (together, the "EHR system action commitment notification data set"). As an example, in the event that a system action direction is sent to the healthcare provider system 102 for the scheduling of a specific laboratory test, upon such scheduling, the healthcare provider system 102 may provide to the data analytics provider system 104 an EHR system action commitment notification to confirm that the system action direction was implemented.

Member Healthcare Gap List Display Removal: Upon receiving a patient encounter end notification and accompanying patient encounter end notification data set, the data analytics provider system 104 may disengage the data analytics provider gap management API and close all associated dialogs, dynamically removing any gap notifications from the graphical user interface of the healthcare provider system.

Informational Dialog: Upon receiving a patient encounter start notification, the data analytics provider system 104 may, via the data analytics provider gap management API or other such API, display a dialog (the "authorized provider member set dialog") to present data and control interfaces pertaining to the authorized provider member. The dialog and its contents may be presented independently or in conjunction with the healthcare gap list notification dialog(s) and/or the healthcare gap dialog(s).

The completion of the elements described above for a patient encounter for which there was one or more healthcare gaps addressed by the healthcare provider may be referred to as a "completed analytically informed EHR encounter." Any patient encounter initiated by a healthcare provider for which a healthcare gap list exists yet a completed analytically informed EHR encounter is not achieved may be referred to as an "incomplete analytically informed EHR encounter." A completed analytically informed EHR encounter followed by a patient data extract for such completed analytically informed EHR encounter is referred to as a "completed analytically informed EHR encounter extract."

Some implementations may involve an ongoing process of real-time interactions that provide one or more of the following registry management functions.

Registry Session Start Notification: Upon an EHR registry administrator indicating their desire to access an EHR registry, the healthcare provider system 102 may facilitate the provision to the data analytics provider 104, in real-time, of notification (the "EHR registry start notification") consisting of the EHR practice ID and EHR registry administrator ID (together, the "EHR registry start notification data").

Registry List Provision: Upon receiving an EHR registry start notification and accompanying EHR registry start notification data set, the data analytics provider system 104 may provide back to healthcare provider system 102, in real-time, either i) a flag indicating that the EHR registry administrator (in consideration with their entire authorized EHR practice universe) has patients with healthcare gaps (the "healthcare gaps present flag"), or ii) a flag indicating that no healthcare gaps are known for such EHR registry administrator nor their entire authorized EHR practice universe (the "no known healthcare gaps flag").

Registry Criteria Selection: Upon receiving a healthcare gaps present flag for the EHR registry administrator, the healthcare provider system 102 may facilitate the activation of an API (the "data analytics provider registry management API") to determine (through the selection of previously defined EHR registry criteria or the creation of new EHR registry criteria) how to display the EHR registry within a displayed dialog box or window.

Selection Dialog: Upon initiation of the data analytics provider registry management API, a dialog may be displayed by which the EHR registry administrator may select from a list of previously defined EHR registry criteria or indicate that a new EHR registry criteria is to be created (the "registry selection dialog").

In the event that a previously defined EHR registry criterion is selected, the criterion may be applied to the applicable EHR practice, the resulting current EHR registry generated, and the EHR registry session may be deemed to have been started.

In the event that the EHR registry administrator indicates the desire to create a new EHR registry criteria, then a series of dialogs may be presented through which the EHR registry administrator may apply search and selection criteria by which specific EHR providers and patients may be included into an EHR registry criteria (the "new registry clinician selection dialog" and "new registry member selection dialog" respectively). Upon the successful determination of a new EHR registry criteria, the EHR registry administrator may indicate the desire to save the new EHR registry criteria (through use of the "EHR registry criteria save dialog"), the EHR registry criteria may be applied to the applicable EHR practice, the resulting current EHR registry generated, and the EHR registry session may be deemed to have been started.

An EHR registry may be utilized for the duration of the EHR registry session (i.e., until such EHR registry session is ended). In some implementations, only one EHR registry session may be in process at any one time by any one EHR registry administrator. As such, only one EHR registry may be active at any one time by any one EHR registry administrator.

Registry Management: Through the data analytics provider registry management API, the EHR registry administrator may be able to select individual patients with individual healthcare gaps within the identified EHR registry. As an individual healthcare gap is selected by the EHR registry administrator, the data analytics provider registry management API will provide a dialog (the "healthcare gap dialog") unique to the patient and respective selected healthcare gap. The healthcare gap dialog will reference the healthcare gap with specific language provided by the data analytics provider to address and potentially resolve the healthcare gap.

As the EHR provider selects individual entries within the healthcare gap list and interacts with the individual healthcare gap dialogs, the data analytics provider system 104 will provide to the healthcare provider system 102 the data required to direct a specific system action within the EHR system 132.

Registry End Notification: Upon the EHR registry administrator indicating their desire to end the EHR registry session (e.g., through the action of selecting a relevant "close" button within a relevant interface), the data analytics provider system 104 may facilitate the provision to healthcare provider system 102, in real-time, of notification (the "EHR registry session end notification") consisting of the EHR practice ID and EHR registry administrator ID (together, the "EHR registry session end notification data set").

Registry Display Removal: Upon receiving an EHR registry session end notification and accompanying EHR registry session end notification data set, the EHR registry session may be deemed ended, and the data analytics provider system 104 may disengage the data analytics provider registry management API and close all associated dialogs.

The messages described above may be sent via any suitable protocol such as, but not limited to, HTTPS over TCP/IP.

Figure 3:
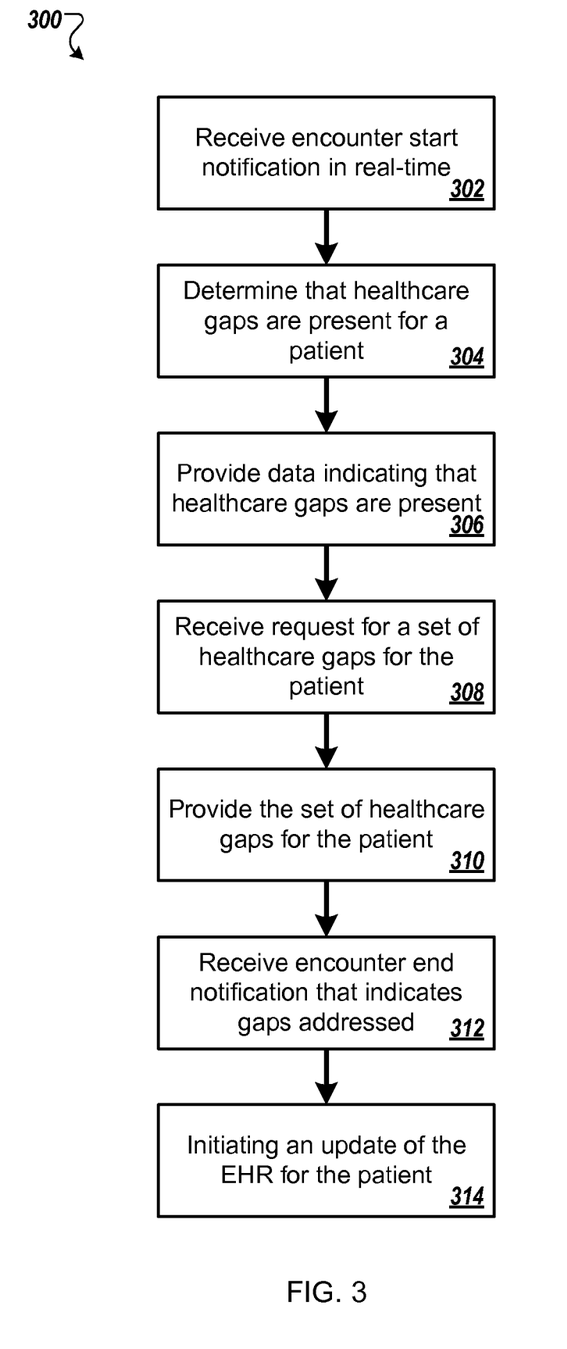
FIG. 3 is an example of a process for real-time healthcare gap management by a data analytics provider.

FIG. 3 shows an example of a process 300 for real-time healthcare gap management by a data analytics provider. The process 300 may be performed by data processing apparatus, such as the data analytics provider system 104 described above or another data processing apparatus.

In stage 302, a data analytics provider system receives an encounter start notification identifying a patient from a healthcare provider system over a network. The encounter start notification is received in real-time (e.g., contemporaneously with) when the patient begins an encounter with a healthcare provider. Then, in stage 304, the data analytics provider system determines that one or more healthcare gaps are present for the patient. This determination may involve, for example, querying a database of healthcare records, querying an index, processing healthcare records to identify gaps, or any suitable combination of these.

Next, in stage 306, the data analytics provider system provides data (e.g., a flag) to the healthcare provider system indicating that healthcare gaps are present for the patient. In response, the data analytics provider system receives a request for a set of healthcare gaps associated with the patient from the healthcare provider system in stage 308. The request for a set of gaps may be triggered, for example, by a patient checking in for their healthcare visit, which is referred to as the "Encounter Start."

The data analytics provider system then provides the healthcare provider system with data representing the set of healthcare gaps associated with the patient in stage 310. The data may be any suitable representation, such as, for example, eXtensible Markup Language (XML) or JavaScript Objection Notation (JSON). The set of healthcare gaps includes at least one entry to be associated with an electronic health record of the patient such that the healthcare provider system can indicate whether one or more of the healthcare gaps were addressed.

In stage 312, the data analytics provider system receives an encounter end notification indicating that the healthcare provider system addressed one or more of the set of healthcare gaps. This encounter end notification is sent in real-time from the healthcare provider when the patient ends the encounter with the healthcare provider. Finally, in stage 314, the data analytics provider initiates an update of the electronic health record of the patient in real-time based on the one or more of the set of healthcare gaps being addressed.

In some implementations, the encounter start notification may form a specific data structure that includes one or more of an electronic health record practice identifier, an electronic health record provider identifier, and a patient identifier. In some implementations, the encounter end notification may form a specific data structure that includes one or more of an electronic health record practice identifier, an electronic health record provider identifier, and a patient identifier.

Figure 4:
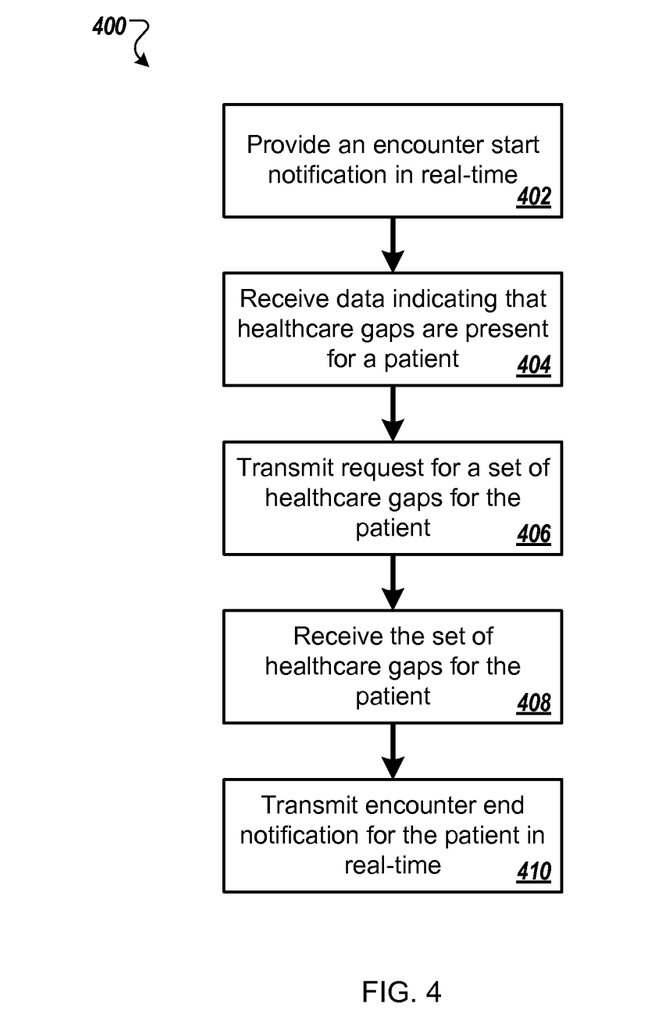
FIG. 4 is an example of a process for real-time healthcare gap management by a healthcare provider.

FIG. 4 shows an example of a process 400 for real-time healthcare gap management by a healthcare provider. The process 400 may be performed by data processing apparatus, such as the healthcare provider system 102 described above or another data processing apparatus.

In stage 402, a healthcare provider system provides a data analytics provider system with an encounter start notification identifying a patient in real-time when the patient begins an encounter with a healthcare provider. The encounter start notification can be sent over any suitable network. Then, in stage 404, the healthcare provider system receives data (e.g., a flag) indicating that healthcare gaps are present for the patient. In response, the healthcare provider system transmits a request for a set of healthcare gaps associated with the patient in stage 406.

Next, in stage 408, the healthcare provider system receives data representing the set of healthcare gaps associated with the patient. The data may be any suitable representation, such as, for example, XML or JSON. The set of healthcare gaps includes at least one entry to be associated with an electronic health record of the patient such that a user of the healthcare provider system can indicate whether one or more of the healthcare gaps were addressed.

Finally, in stage 410, the healthcare provider system sends an encounter end notification to the data analytics provider in real-time when the patient ends the encounter with the healthcare provider. The encounter end notification indicates that the healthcare provider system addressed one or more of the set of healthcare gaps.

In some implementations, the encounter start notification comprises one or more of an electronic health record practice identifier, an electronic health record provider identifier, and a patient identifier. In some implementations, the encounter end notification comprises one or more of an electronic health record practice identifier, an electronic health record provider identifier, and a patient identifier.

Some implementations involve the additional step of providing for display data representing the set of healthcare gaps. For example, an employee of the healthcare provider operating a client device may be shown a user interface that displays a table or collection of healthcare gaps for the patient.

Some implementations involve the additional step of determining that at least one healthcare gap from the set of healthcare gaps has been addressed. For example, the healthcare provider system may determine that a required diagnostic test has been order, or a missing diagnosis has been added to the patient's record. The at least one gap may be a gap in care and/or a gap in documentation.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

The computing system can include clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described.

Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A non-transitory computer-readable medium storing instructions executable by one or more computers which, upon such execution, cause the one or more computers to perform operations comprising:

receiving, at a data analytics provider server of a healthcare gap management system that includes (a) the data analytics provider server, (b) a healthcare provider server associated with a healthcare provider, (c) a mobile computing device that includes a global positioning system (GPS) sensor and that is associated with the healthcare provider server, (d) medical diagnostic equipment that is associated with the healthcare provider, and (e) an electronic health record server, and from the healthcare provider server over a network, an encounter start notification (i) indicating that an encounter the healthcare provider has begun, (ii) identifying a patient, and (iii) being received in real-time to when GPS sensor data generated by the GPS sensor of the mobile computing device that is associated with the healthcare provider server indicates that a location of the mobile computing device matches a location that is associated with a healthcare provider;

before receiving an encounter end notification indicating that the encounter between the patient and the healthcare provider has ended, determining, at the data analytics provider server of the healthcare gap management system, that one or more healthcare gaps that were identified by the data analytics provider server of the healthcare gap management system before receiving the encounter start notification are present for the patient, wherein a healthcare gap comprises a difference between a recommended treatment protocol and an actual course of treatment for a diagnosed condition, or a difference between an actual course of treatment and a diagnosis that corresponds to that course of treatment;

before receiving an encounter end notification indicating that the encounter between the patient and the healthcare provider has ended, providing, from the data analytics provider server of the healthcare gap management system to the healthcare provider server of the healthcare gap management system, data indicating that one or more healthcare gaps that were identified by the data analytics provider server of the healthcare gap management system before receiving the encounter start notification are indicated as present for the patient;

before receiving an encounter end notification indicating that the encounter between the patient and the healthcare provider has ended, receiving, at the data analytics provider server of the healthcare gap management system and from the healthcare provider server of the healthcare gap management system, a request for data identifying one or more of the healthcare gaps that were identified by the data analytics provider server of the healthcare gap management system before receiving the encounter start notification and that are indicated as presented for the patient;

before receiving an encounter end notification indicating that the encounter between the patient and the healthcare provider has ended, providing, from the data analytics provider server of the healthcare gap management system to the healthcare provider server of the healthcare gap management system, data identifying one or more of the healthcare gaps that were identified by the data analytics provider server of the healthcare gap management system before receiving the encounter start notification and that are indicated as present for the patient, wherein the data identifying the one or more of the healthcare gaps that were identified by the data analytics provider server of the healthcare gap management system before receiving the encounter start notification and that are indicated as present for the patient includes at least one entry to be associated with an electronic health record of the patient, wherein the at least one entry to be associated with the electronic health record of the patient enables the healthcare gap management system to indicate whether one or more of the healthcare gaps that were identified by the data analytics provider server of the healthcare gap management system before receiving the encounter start notification and that are indicated as present for the patient was at least partially addressed;

receiving, at the data analytics provider server of the healthcare gap management system from the healthcare provider server of the healthcare gap management system, an encounter end notification indicating that the encounter between the patient and the healthcare provider has ended and that the healthcare provider server of the healthcare gap management system at least partially addressed one or more of the healthcare gaps that were identified by the data analytics provider server of the healthcare gap management system before receiving the encounter start notification and that are indicated as present for the patient by performing one or more additional tests using the medical diagnostic equipment of the healthcare gap management system; and updating, by the electronic health record server of the healthcare gap management system, the electronic health record of the patient in real-time based on the received encounter end notification indicating that the healthcare provider server of the healthcare gap management system at least partially addressed one or more of the healthcare gaps that were identified by the data analytics provider server of the healthcare gap management system before receiving the encounter start notification and that are indicated as present for the patient by performing the one or more additional tests using the medical diagnostic equipment of the healthcare gap management system.

2. The computer-readable medium of claim 1, wherein the encounter start notification comprises one or more of an electronic health record practice identifier, an electronic health record provider identifier, and a patient identifier.

3. The computer-readable medium of claim 1, wherein the encounter end notification comprises one or more of an electronic health record practice identifier, an electronic health record provider identifier, and a patient identifier.

4. The computer-readable medium of claim 1, wherein determining, at the data analytics provider server of the healthcare gap management system, that one or more healthcare gaps that were identified by the data analytics provider server of the healthcare gap management system before receiving the encounter start notification are present for the patient comprises querying, by the data analytics provider server of the healthcare gap management system, a healthcare database of the healthcare gap management system to determine that one or more healthcare gaps that were identified by the data analytics provider server of the healthcare gap management system before receiving the encounter start notification are present for the patient.

5. A non-transitory computer-readable medium storing instructions executable by one or more computers which, upon such execution, cause the one or more computers to perform operations comprising:

determining, at a healthcare provider server that is associated with a healthcare provider and that is of a healthcare gap management system that includes (a) a data analytics provider server, (b) the healthcare provider server, (c) a mobile computing device that includes a global positioning system (GPS) sensor and that is associated with the healthcare provider server, (d) medical diagnostic equipment that is associated with the healthcare provider, and (e) an electronic health record server, and based on GPS sensor data generated the GPS sensor of the mobile computing device of the healthcare gap management system indicating that a location of the mobile computing device matches a location that is associated with a healthcare provider, that a patient has begun an encounter with the healthcare provider;

in response to determining that the patient has begun the encounter with the healthcare provider, providing, from the healthcare provider server of the healthcare gap management system to the data analytics provider server of the healthcare gap management system over a network, an encounter start notification identifying the patient in real-time when the patient begins the encounter with the healthcare provider;

before the encounter between the patient and the healthcare provider has ended, receiving, at the healthcare provider server of the healthcare gap management system from the data analytics provider server of the healthcare gap management system, data indicating that one or more healthcare gaps that were identified by the data analytics provider server of the healthcare gap management system before the encounter between the patient and the healthcare provider began are present for the patient, wherein a healthcare gap comprises a difference between a recommended treatment protocol and an actual course of treatment for a diagnosed condition, or a difference between an actual course of treatment and a diagnosis that corresponds to that course of treatment;

before the encounter between the patient and the healthcare provider has ended, providing, from the healthcare provider server of the healthcare gap management system to the data analytics provider server of the healthcare gap management system, a request for data identifying one or more of the healthcare gaps that were identified by the data analytics provider server of the healthcare gap management system before the encounter between the patient and the healthcare provider began and that are indicated as present for the patient;

before the encounter between the patient and the healthcare provider has ended, receiving, at the healthcare provider server of the healthcare gap management system from the data analytics provider server of the healthcare gap management system, data identifying one or more of the healthcare gaps that were identified by the data analytics provider server of the healthcare gap management system before the encounter between the patient and the healthcare provider began and that are indicated as present for the patient;

before the encounter between the patient and the healthcare provider has ended, receiving, at the healthcare provider server of the healthcare gap management system, a selection of a control for initiating one or more additional tests using the medical diagnostic equipment of the healthcare gap management system, to at least partially address one or more of the healthcare gaps that were identified by the data analytics provider server of the healthcare gap management system before the encounter between the patient and the healthcare provider began and that are indicated as present for the patient;

before the encounter between the patient and the healthcare provider has ended and in response to the selection of the control, performing one or more of the additional tests using the medical diagnostic equipment of the healthcare gap management system to at least partially address one or more of the healthcare gaps that were identified by the data analytics provider server of the healthcare gap management system before the encounter between the patient and the healthcare provider began and that are indicated as present for the patient;

determining, based on additional sensor data generated by the mobile computing device of the healthcare gap management system, that the encounter between the patient and the healthcare provider has ended or likely ended; and in response to determining, based on the additional sensor data generated by the mobile computing device of the healthcare gap management system, that the encounter between the patient and the healthcare provider has ended or likely ended, providing, from the healthcare provider server of the healthcare gap management system to the data analytics provider server of the healthcare gap management system, an encounter end notification in real-time to when the patient ends the encounter with the healthcare provider, the encounter end notification indicating that the healthcare provider server of the healthcare gap management system addressed one or more of the healthcare gaps that were identified by the data analytics provider server of the healthcare gap management system before the encounter between the patient and the healthcare provider began and that are indicated as present for the patient as a result of performing the one or more additional tests using the medical diagnostic equipment of the healthcare gap management system.

6. The computer-readable medium of claim 5, wherein the encounter start notification comprises one or more of an electronic health record practice identifier, an electronic health record provider identifier, and a patient identifier.

7. The computer-readable medium of claim 5, wherein the encounter end notification comprises one or more of an electronic health record practice identifier, an electronic health record provider identifier, and a patient identifier.

8. The computer-readable medium of claim 5, wherein the operations further comprise providing, for display, data representing the one or more of the healthcare gaps that were identified by the data analytics provider server of the healthcare gap management system before the encounter between the patient and the healthcare provider began and that are indicated as present for the patient.

9. The computer-readable medium of claim 5, wherein the operations further comprise determining that at least one of the one or more of the healthcare gaps that were identified by the data analytics provider server of the healthcare gap management system before the encounter between the patient and the healthcare provider began and that are indicated as present for the patient has been at least partially addressed based on the performance of the one or more of the additional tests using the medical diagnostic equipment of the healthcare gap management system.

10. The computer-readable medium of claim 5, wherein the one or more healthcare gaps that were identified by the data analytics provider server of the healthcare gap management system before the encounter between the patient and the healthcare provider began and that are indicated as present for the patient include a gap in care.

11. The computer-readable medium of claim 5, wherein the one or more healthcare gaps that were identified by the data analytics provider server of the healthcare gap management system before the encounter between the patient and the healthcare provider began and that are indicated as present for the patient include a gap in documentation.

12. A healthcare gap management system comprising:
a data analytics provider server;
a healthcare provider server associated with a healthcare provider;
a mobile computing device that includes a global positioning system (GPS) sensor and that is associated with the healthcare provider server;
medical diagnostic equipment that is associated with the healthcare provider;
an electronic health record server; and
one or more storage devices storing instructions that are operable, when executed by one or more of the servers, to cause the one or more computers servers to perform operations comprising:
receiving, at the data analytics provider server of the healthcare gap management system from a healthcare provider server of the healthcare gap management system over a network, an encounter start notification (i) indicating that an encounter with a healthcare provider has begun, (ii) identifying a patient, and (iii) being received in real-time to when GPS sensor data generated the GPS sensor of the mobile computing device of the healthcare gap management system indicates that a location of the mobile computing device matches a location that is associated with the healthcare provider;
before receiving an encounter end notification indicating that the encounter between the patient and the healthcare provider has ended, determining, at the data analytics provider server of the healthcare gap management system, that one or more healthcare gaps that were identified by the data analytics provider server of the healthcare gap management system before receiving the encounter start notification are present for the patient, wherein a healthcare gap comprises a difference between a recommended treatment protocol and an actual course of treatment for a diagnosed condition, or a difference between an actual course of treatment and a diagnosis that corresponds to that course of treatment;
before receiving an encounter end notification indicating that the encounter between the patient and the healthcare provider has ended, providing, from the data analytics provider server of the healthcare gap management system to the healthcare provider server of the healthcare gap management system, data indicating that one or more healthcare gaps that were identified by the data analytics provider server of the healthcare gap management system before receiving the encounter start notification are indicated as present for the patient;
before receiving an encounter end notification indicating that the encounter between the patient and the healthcare provider has ended, receiving, at the data analytics provider server of the healthcare gap management system from the healthcare provider server of the healthcare gap management system, a request for data identifying one or more of the healthcare gaps that were identified by the data analytics provider server of the healthcare gap management system before receiving the encounter start notification and that are indicated as presented for the patient;
before receiving an encounter end notification indicating that the encounter between the patient and the healthcare provider has ended, providing, from the data analytics provider server of the healthcare gap management system to the healthcare provider server of the healthcare gap management system, data identifying one or more of the healthcare gaps that were identified by the data analytics provider server of the healthcare gap management system before receiving the encounter start notification and that are indicated as present for the patient, wherein the data identifying the one or more of the healthcare gaps that were identified by the data analytics provider server of the healthcare gap management system before receiving the encounter start notification and that are indicated as present for the patient includes at least one entry to be associated with an electronic health record of the patient, wherein the at least one entry to be associated with the electronic health record of the patient enables the healthcare gap management system to indicate whether one or more of the healthcare gaps that were identified by the data analytics provider server of the healthcare gap management system before receiving the encounter start notification and that are indicated as present for the patient was at least partially addressed;

receiving, at the data analytics provider server of the healthcare gap management system from the healthcare provider server of the healthcare gap management system, an encounter end notification indicating that the encounter between the patient and the healthcare provider has ended and that the healthcare provider server of the healthcare gap management system at least partially addressed one or more of the healthcare gaps that were identified by the data analytics provider server of the healthcare gap management system before receiving the encounter start notification and that are indicated as present for the patient by performing one or more additional tests using the medical diagnostic equipment of the healthcare gap management system; and updating, by the electronic health record server of the healthcare gap management system, the electronic health record of the patient in real-time based on the received encounter end notification indicating that the healthcare provider server of the healthcare gap management system at least partially addressed one or more of the healthcare gaps that were identified by the data analytics provider server of the healthcare gap management system before receiving the encounter start notification and that are indicated as present for the patient by performing the one or more additional tests using the medical diagnostic equipment of the healthcare gap management system.

13. The system of claim 12, wherein the encounter start notification comprises one or more of an electronic health record practice identifier, an electronic health record provider identifier, and a patient identifier.

14. The system of claim 12, wherein the encounter end notification comprises one or more of an electronic health record practice identifier, an electronic health record provider identifier, and a patient identifier.

15. A healthcare gap management system comprising:
a data analytics provider server;
a healthcare provider server associated with a healthcare provider;
a mobile computing device that includes a global positioning system (GPS) sensor and that is associated with the healthcare provider server;
medical diagnostic equipment that is associated with the healthcare provider;
an electronic health record server; and
one or more storage devices storing instructions that are operable, when executed by one or more of the servers, to cause the one or more servers to perform operations comprising:

determining, at the healthcare provider server and based on GPS sensor data generated the GPS sensor of the mobile computing device of the healthcare gap management system indicating that a location of the mobile computing device matches a location that is associated with a healthcare provider, that a patient has begun an encounter with the healthcare provider;

in response to determining that the patient has begun the encounter with the healthcare provider, providing, from the healthcare provider server of the healthcare gap management system to the data analytics provider server of the healthcare gap management system over a network, an encounter start notification identifying the patient in real-time when the patient begins the encounter with the healthcare provider;

before the encounter between the patient and the healthcare provider has ended, receiving, at the healthcare provider server of the healthcare gap management system from the data analytics provider server of the healthcare gap management system, data indicating that one or more healthcare gaps that were identified by the data analytics provider server of the healthcare gap management system before the encounter between the patient and the healthcare provider began are present for the patient, wherein a healthcare gap comprises a difference between a recommended treatment protocol and an actual course of treatment for a diagnosed condition, or a difference between an actual course of treatment and a diagnosis that corresponds to that course of treatment;

before the encounter between the patient and the healthcare provider has ended, providing, from the healthcare provider server of the healthcare gap management system to the data analytics provider server of the healthcare gap management system, a request for data identifying one or more of the healthcare gaps that were identified by the data analytics provider server of the healthcare gap management system before the encounter between the patient and the healthcare provider began and that are indicated as present for the patient;

before the encounter between the patient and the healthcare provider has ended, receiving, at the healthcare provider server of the healthcare gap management system from the data analytics provider server of the healthcare gap management system, data identifying one or more of the healthcare gaps that were identified by the data analytics provider server of the healthcare gap management system before the encounter between the patient and the healthcare provider began and that are indicated as present for the patient;

before the encounter between the patient and the healthcare provider has ended, receiving, at the healthcare provider server of the healthcare gap management system, a selection of a control for initiating one or more additional tests using the medical diagnostic equipment of the healthcare gap management system, to at least partially address one or more of the healthcare gaps that were identified by the data analytics provider server of the healthcare gap management system before the encounter between the patient and the healthcare provider began and that are indicated as present for the patient;

before the encounter between the patient and the healthcare provider has ended and in response to the selection of the control, performing one or more of the additional tests using the medical diagnostic equipment of the healthcare gap management system to at least partially address one or more of the healthcare gaps that were identified by the data analytics provider server of the healthcare gap management system before the encounter between the patient and the healthcare provider began and that are indicated as present for the patient;

determining, based on additional sensor data generated by the mobile computing device of the healthcare gap management system, that the encounter between the patient and the healthcare provider has ended or likely ended; and in response to determining, based on the additional sensor data generated by the mobile computing device of the healthcare gap management system, that the encounter between the patient and the healthcare provider has ended or likely ended, providing, from the healthcare provider server of the healthcare gap management system to the data analytics provider server of the healthcare gap management system, an encounter end notification in real-time to when the patient ends the encounter with the healthcare provider, the encounter end notification indicating that the healthcare provider server of the healthcare gap management system addressed one or more of the healthcare gaps that were identified by the data analytics provider server of the healthcare gap management system before the encounter between the patient and the healthcare provider began and that are indicated as present for the patient as a result of performing the one or more additional tests using the medical diagnostic equipment of the healthcare gap management system.

16. The system of claim 15, wherein the encounter start notification comprises one or more of an electronic health record practice identifier, an electronic health record provider identifier, and a patient identifier.

17. The system of claim 15, wherein the encounter end notification comprises one or more of an electronic health record practice identifier, an electronic health record provider identifier, and a patient identifier.

18. The system of claim 15, wherein the operations further comprise providing, for display, data representing the one or more of the healthcare gaps that were identified by the data analytics provider server of the healthcare gap management system before the encounter between the patient and the healthcare provider began and that are indicated as present for the patient.

19. The system of claim 15, wherein the operations further comprise determining that at least one of the one or more of the healthcare gaps that were identified by the data analytics provider server of the healthcare gap management system before the encounter between the patient and the healthcare provider began and that are indicated as present for the patient has been at least partially addressed based on the performance of the one or more of the additional tests using the medical diagnostic equipment of the healthcare gap management system.

20. The system of claim 15, wherein the one or more healthcare gaps that were identified by the data analytics provider server of the healthcare gap management system before the encounter between the patient and the healthcare provider began and that are indicated as present for the patient include a gap in care.

* * * * *

UNITED STATES PATENT AND TRADEMARK OFFICE
CERTIFICATE OF CORRECTION

PATENT NO.       : 9,710,600 B1
APPLICATION NO.  : 14/886876
DATED            : July 18, 2017
INVENTOR(S)      : Keith R. Dunleavy et al.

Page 1 of 1

It is certified that error appears in the above-identified patent and that said Letters Patent is hereby corrected as shown below:

In the Claims

Column 20, Line 15, delete "computers".

Signed and Sealed this
Seventh Day of November, 2017

Joseph Matal
*Performing the Functions and Duties of the*
*Under Secretary of Commerce for Intellectual Property and*
*Director of the United States Patent and Trademark Office*